US004001585B2

United States Statutory Invention Registration [19]

[11] Reg. Number: H1585

[45] Published: Aug. 6, 1996

Ahr

[54] ABSORBENT ARTICLE HAVING A BRAIDED WICKING STRUCTURE

[76] Inventor: Nicholas A. Ahr, 6100 Center Hill Rd., Cincinnati, Ohio 45224

[21] Appl. No.: 268,894

[22] Filed: Jun. 30, 1994

[51] Int. Cl.[6] ..... A61F 13/15

[52] U.S. Cl. ..... 604/378; 604/384; 604/381

[58] Field of Search ..... 604/378, 366, 604/370, 384, 381, 385.1

[56] References Cited

U.S. PATENT DOCUMENTS

| | | | |
|---|---|---|---|
| Re. 26,515 | 1/1969 | Holliday et al. | 604/370 |
| 810,129 | 1/1906 | Green . | |
| 1,950,765 | 3/1934 | Winter . | |
| 2,551,663 | 5/1951 | Fox . | |
| 2,581,561 | 6/1947 | Shaw . | |
| 2,929,179 | 3/1960 | George . | |
| 3,343,543 | 9/1967 | Glassman . | |
| 3,356,092 | 12/1967 | Joa . | |
| 3,523,535 | 8/1970 | Croon . | |
| 3,716,430 | 2/1973 | Croon . | |
| 3,736,931 | 6/1973 | Glassman . | |
| 3,844,288 | 10/1974 | Kiela . | |
| 4,324,246 | 4/1982 | Mullane et al. | 604/384 |
| 4,361,151 | 11/1982 | Fitzgerald . | |
| 4,762,520 | 8/1988 | Wallstrom . | |
| 5,002,814 | 3/1991 | Knack et al. . | |
| 5,200,248 | 4/1993 | Thompson et al. . | |

FOREIGN PATENT DOCUMENTS

| | | | |
|---|---|---|---|
| 391814 | 10/1990 | European Pat. Off. . | |
| 0391814A2 | 10/1990 | European Pat. Off. . | |
| 513876 | 12/1930 | Germany | 604/384 |
| 410702 | 5/1934 | United Kingdom . | |
| WO91/16870 | 11/1991 | WIPO . | |

*Primary Examiner*—Michael J. Carone
*Assistant Examiner*—Theresa M. Wesson

[57] ABSTRACT

An absorbent article, such as a sanitary napkin is provided. The sanitary napkin of the present invention has a substantially non-absorbent braided wicking structure.

1 Claim, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ABSORBENT ARTICLE HAVING A BRAIDED WICKING STRUCTURE

FIELD OF THE INVENTION

The present invention relates to absorbent articles, especially catamenial articles such as sanitary napkins. More particularly, this invention is directed to a sanitary napkin having a braided witking structure.

BACKGROUND OF THE INVENTION

A wide variety of types of structures for disposable absorbent articles used to collect body fluids are known in the art. Commercial absorbent articles include diapers, adult incontinence products, catamenials and bandages. Disposable products of this type comprise components for receiving, absorbing and retaining fluids. Typically, such articles include a liquid permeable topsheet, an absorbent core and a liquid impermeable backsheet.

One of the main objectives in developing absorbent articles is to utilize the entire capacity of the absorbent article. In general, products of the type described above typically distribute liquids deposited on the topsheet in a circular pattern. Since such structures generally have a length that exceeds their width, this results in liquids reaching the longitudinal side edges of the absorbent article before the end regions of the absorbent article are fully utilized. When liquids reach the longitudinal side edges of the absorbent article, this increases the chance for leakage from the sides of the product, despite available absorbent capacity in the end regions of the absorbent article.

In the past, a number of efforts have been made to direct the flow of exudates in an attempt to utilize more of the absorbent capacity of an absorbent article. A number of these efforts have used absorbent means or densification of absorbent means. Some of such efforts are described in U.S. Pat. No. 4,678,453 issued Jul. 7, 1987 to Holtman and U.S. Pat. No. 4,624,666 issued Nov. 25, 1986 to DeRossett, et al. Absorbent articles which use absorbent means to direct exudate flow, however, are typically subject to the disadvantage that the absorbent means will tend to become saturated which interferes with its liquid directing capabilities.

The better distribution and utilization of the capacity for absorption of menses and other bodily exudates in thin sanitary napkins having capacities great enough to handle medium to high menstrual flows is disclosed in U.S. Pat. Nos. 4,950,264 and 5,009,653, issued to Osborn, on Aug. 21, 1990 and Apr. 23, 1991, respectively. The distribution of exudates in the sanitary napkins described in these references is achieved at least in part by using a "wipe acquisition sheet" that distributes the exudates more evenly over an underlying absorbent core.

Still other sanitary napkins have been developed which use fibers having intra-fiber capillary channels, particularly on their exterior surfaces for transporting liquids. Examples of such sanitary napkins are disclosed in PCT International Publication Nos. WO 93/01779 to WO 93/01783 and WO 93/02251, all of which publications are incorporated by reference herein. Several of these publications disclose sanitary napkins that use capillary channel fibers that may be arranged in the form of a tufted bundle (or "bun"). The sanitary napkins described in these international patent publications work quite well. However, capillary channel fibers can be quite expensive for use in disposable absorbent articles. Therefore, the search for alternative sanitary napkins has continued.

Still other types of absorbent structures are known in the art. For example, U.S. Pat. No. 4,361,151 issued to Fitzgerald discloses a tampon formed from braided slivers of absorbent material. The braided structure in the Fitzgerald tampon is hydrophilic and serves as the primary absorbent component of the tampon. The Fitzgerald patent, however, does not disclose a sanitary napkin or a structure for improving the utilization of the entire capacity of a sanitary napkin.

Thus, a need exists for a sanitary napkin having an alternative type of liquid distribution mechanism for directing liquids to better utilize the entire capacity of the sanitary napkin, and particularly to one that does not use an absorbent mechanism for liquid distribution.

It is, therefore, an object of the present invention to provide disposable absorbent articles that have an improved mechanism for distributing the exudates throughout the absorbent core of the article.

It is another object of the present invention to provide absorbent articles that have a mechanism for distributing body exudates that will not become saturated and interfere with its liquid distribution capability.

It is another object of the present invention to provide absorbent articles having the above characteristics which are easily and inexpensively manufactured.

These and other objects of the present invention will be more readily apparent when considered in reference to the following description and when taken in conjunction with the accompanying drawings.

SUMMARY OF THE INVENTION

The present invention provides an absorbent article, such as a sanitary napkin having a braided wicking structure.

The sanitary napkin has a body side, a garment side, a longitudinal centerline, and a transverse centerline. The sanitary napkin comprises a liquid pervious topsheet, a liquid impervious backsheet joined to the topsheet, an absorbent core, and at least one braided wicking structure positioned between the topsheet and backsheet. The braided wicking structure is preferably substantially non-absorbent (i.e., it does not absorb and permanently retain liquids) and transports liquids along its length and empties such liquids into the absorbent core.

DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

1. General Characteristics of the Absorbent Article

Figure 1:
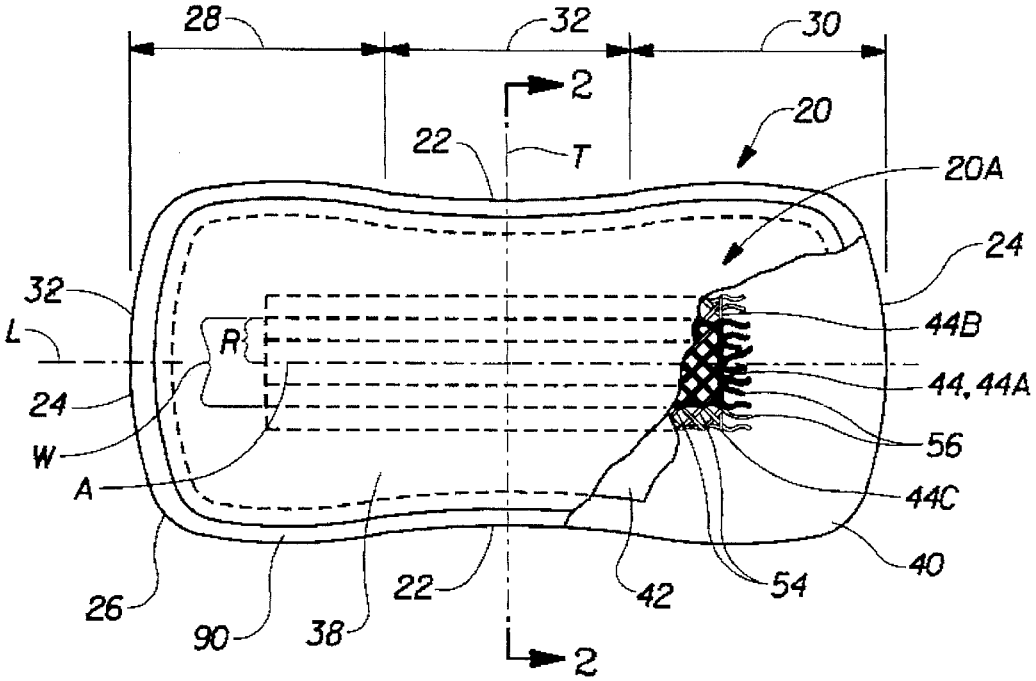
FIG. 1 is a plan view (partially cut away) of a preferred sanitary napkin according to the present invention.
Figure 2:
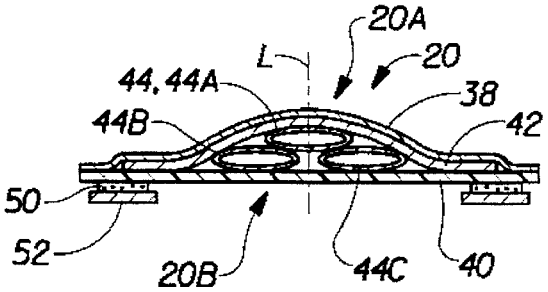
FIG. 2 is a cross section of the sanitary napkin shown in FIG. 1 taken along line 2—2.

A preferred embodiment of the disposable absorbent article of the present invention is the sanitary napkin 20, shown in FIGS. 1 and 2. It should be understood that the present invention is not limited to sanitary napkins having the specific configurations shown in the drawings. The present invention is also applicable to other feminine hygiene or catamenial pads such as pantiliners, or other absorbent articles such as diapers, incontinence pads, and the like.

The sanitary napkin 20 shown in FIGS. 1 and 2 has two surfaces, a body-contacting surface or "body surface" 20A and a garment surface 20B. The sanitary napkin 20 is shown in FIG. 1 as viewed from its body surface 20A. The body surface 20A is intended to be worn adjacent to the body of the wearer while the garment surface 20B (shown in FIG. 2) is on the opposite side and is intended to be placed adjacent to the wearer's undergarments when the sanitary napkin 20 is worn.

The sanitary napkin 20 has two centerlines, a longitudinal centerline, L, and a transverse centerline, T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 also shows that the sanitary napkin 20 has a periphery 26 which is defined by the outer edges of the sanitary napkin 20 in which the longitudinal edges (or "side edges") are designated 22 and the end edges (or "ends") are designated 24. The sanitary napkin has two end regions, which are designated first end region 28 and second end region 30. A central region 32 is disposed between the end regions 28 and 30. The end regions 28 and 30 extend outwardly from the edges of the central region 32 about ⅛ to about ⅓ of the length of the sanitary napkin. A detailed description of the central region 32 and the two end regions 28 and 30 is contained in U.S. Pat. No. 4,690,680 issued to Higgins on Sep. 1, 1987.

The sanitary napkin 20 preferably comprises a liquid pervious topsheet 38, a liquid impervious backsheet 40 joined to the topsheet 38, an absorbent core 42 positioned between the topsheet 38 and the backsheet 40, and one or more braided wicking structures 44. The sanitary napkin 20 can also be provided with one or more additional layers or components. These may include a wicking layer or secondary topsheet. The wicking layer or secondary topsheet can be either an integral part of the topsheet or a separate component positioned between the topsheet and absorbent core. The sanitary napkin 20 may also include at least one panty fastener, such as panty fastening adhesive strips 50 (shown in FIGS. 2 and 3). An optional release paper 52 may cover the adhesive strips 50. The release paper 52 keeps the adhesives 50 from sticking to surfaces other than the crotch portion of the undergarment prior to use of the sanitary napkin 20. These individual components of the sanitary napkin will now be looked at in greater detail.

2. The Individual Components of the Sanitary Napkin

A. The Topsheet

The topsheet 38, as shown in FIGS. 1 and 2, is the component which is intended to be oriented towards and contact the body of the wearer, and to initially receive bodily discharges.

The topsheet 38 is liquid pervious and should be flexible and non-irritating to the skin. As used herein the term "flexible" refers to materials which are compliant and readily conform to the shape of the body or respond by easily deforming in the presence of external forces. The topsheet 38 should exhibit good strikethrough and low rewet characteristics, permitting bodily discharges to rapidly penetrate the thickness of the topsheet 38 and move into the absorbent core 42, but not flow back through the topsheet 38 to the skin of the wearer. Preferably, the topsheet 38 is not noisy, to provide discretion for the wearer. The topsheet 38 should be sanitary, clean in appearance and somewhat opaque to hide bodily discharges collected in and absorbed by the absorbent core 42.

A suitable topsheet 38 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; thermoplastic scrims; or composites of any of the foregoing types of materials. Suitable woven and nonwoven materials can be comprised of natural fibers (e.g., wood or cotton fibers), synthetic fibers (e.g., polymefic fibers such as polyester, polypropylene, or polyethylene fibers) or from a combination of natural and synthetic fibers.

A preferred topsheet 38 comprises an apertured formed film. Apertured formed films are preferred for the topsheet because they are pervious to body exudates, yet nonabsorbent, and if properly apertured have a reduced tendency to allow liquids to pass back through and rewet the wearer's skin. Thus, the surface of the formed film which is in contact with the body remains dry, thereby reducing body soiling and creating a more comfortable feel for the wearer.

Suitable formed films are described in U.S. Pat. No. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel, et al. on Aug. 3, 1982; U.S. Pat. No. 4,463,045 issued to Ahr, et al. on Jul. 31, 1984; U.S. Pat. No. 4,629,643 issued to Curro, et al. on Dec. 16, 1986; and U.S. Pat. No. 5,006,394 issued to Baird on Apr. 9, 1991. The preferred topsheet for the present invention is the formed film described in one or more of the above patents and marketed on sanitary napkins by The Procter & Gamble Company as "DRIWEAVE".

In a preferred embodiment, the topsheet 38 is hydrophilic so that liquids will transfer through the topsheet 38 faster than if it was not hydrophilic. This will diminish the likelihood that body exudates will flow off the topsheet rather than being absorbed by the absorbent core. Such topsheets (as well as fibrous topsheets) can be rendered hydrophilic by treating them with surfactants. Suitable methods of applying surfactants are described in U.S. Pat. Nos. 4,950,254 and 5,009,653 issued to Osborn.

B. The Absorbent Core (1) General

The absorbent core 42 is an absorbent means which is capable of absorbing and retaining liquids such as vaginal fluids (e.g., menses) and other body exudates. As shown in FIGS. 1 and 2, the absorbent core 42 has a body surface, a garment surface, side edges, and end edges.

The absorbent core 42 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles.

Suitable materials for the absorbent core 42 include but are not limited to: comminuted wood pulp, which is generally referred to as airfelt; creped cellulose wadding; tissue including tissue wraps and tissue laminates; synthetic fibers, especially polymeric fibers, such as crimped polyester fibers; meltblown polymers including coform; chemically stiflened, modified or cross-linked cellulosic fibers; fibers have intra-fiber capillary channels preferably on their exterior surfaces (capillary channel fibers); peat moss; absorbent foams; absorbent sponges; superabsorbent hydrogel-forming polymeric gelling agents; or any equivalent materials, combinations, or mixtures of these materials.

Suitable cross-linked cellulose fibers are described in greater detail in U.S. Pat. No. 5,217,445 issued to Young, et al. on Jun. 8, 1993. Suitable capillary channel fibers are described in U.S. Pat. No. 5,200,248 issued to Thompson, et al. on Apr. 6, 1993. Suitable foam materials are described in U.S. Pat. No. 5,147,345 issued to Young, et al. on Sep. 15, 1992 and in U.S. Pat. Nos. 5,260,345 and 5,268,224 issued to DesMarais, et al. on Nov. 9, 1993 and Dec. 7, 1993, respectively.

Polymeric gelling agents are particularly preferred absorbent materials for use in the absorbent core 42. Polymeric gelling agents are those materials which, upon contact with fluids (i.e., liquids) such as water or body fluids, imbibe such fluids and thereby form hydrogels. In this manner, fluid discharged into the absorbent core 42 can be acquired and held by the polymeric gelling agent, thereby providing the absorbent articles described herein with enhanced absorbent capacity and/or improved fluid retention performance. Suitable absorbent gelling materials are described in U.S. Pat. Re. No. 32,649 issued Apr. 19, 1988 to Brandt et al. and U.S. Pat. No. 5,102,597 issued to Roe, et al. on Apr. 7, 1992. A suitable laminate of absorbent gelling materials and tissue may be purchased from Grain Processing Corporation of Muscatine, Iowa under Model Number L535.

Various examples of absorbent structures suitable for use as the absorbent core of the present invention are described in: U.S. Pat. No. 4,578,068 entitled "Absorbent Laminate Structure" issued to Kramer, et al. on Mar. 25, 1986; U.S. Pat. No. 4,610,678 entitled "High-Density Absorbent Structures" issued to Weisman et al. on Sep. 9, 1986; U.S. Pat. No. 4,640,810 entitled "System for Producing an Airlaid Web" issued to Laursen, et al. Feb. 3, 1987; U.S. Pat. No. 4,834,735 entitled "High Density Absorbent Members Having Lower Density and Lower Basis Weight Acquisition Zones", issued to Alemany et al. on May 30, 1989; U.S. Pat. Nos. 4,950,264 and 5,009,653 entitled "Thin, Flexible Sanitary Napkin" issued to Osborn on Aug. 21, 1990 and Apr. 23, 1991; European Patent Application No. 0 198.683, published Oct. 22, 1986 in the name of Duenk, et al.; and in U.S. patent application Ser. No. 07/810,774 and its continuation-in-part, Ser. No. 07/944,764 both entitled "Absorbent Article Having Fused Layers" filed in the name of Cree, et al. on Dec. 17, 1991 and Sep. 14, 1992, respectively (PCT Patent Publication No. WO 93/11725), which have now been combined in U.S. patent application Ser. No. 08/239,084 filed May 6, 1994.

The configuration and construction of the absorbent core 42 may be varied in different embodiments. For example, the absorbent core may have: varying caliper zones (e.g., the core may be profiled so as to be thicker in the center); hydrophilic gradients; superabsorbent gradients, or lower density and lower average basis weight acquisition zones; or it may comprise one or more layers or structures. The total absorbent capacity of the absorbent core 42 should, however, be compatible with the design loading and the intended use of the sanitary napkin 20. Further, the size and absorbent capacity of the absorbent core 42 may be varied to accommodate different uses such as incontinence pads, pantiliners, regular sanitary napkins, or overnight sanitary napkins.

(2) The Cross-Linked Cellulose Fiber Laminate Core

One particularly preferred absorbent core 42 is a laminate that is comprised of a layer of superabsorbent polymeric material (or absorbent gelling material) and one or more sheets or webs of cross-linked cellulosic fibers. Preferably, the absorbent gelling material in such a laminate structure is placed between two layers of cross-linked cellulosic fibers.

The layers of cross-linked cellulosic fibers in such an embodiment may comprise a single sheet that wraps a layer of particles of absorbent gelling material. The sheet may be wrapped so that it appears as having an "e" configuration when viewed from the end. The wrapped sheet thereby forms an upper layer and a lower layer. In alternative embodiments, the laminate can be formed in many other manners, such as by providing separate webs of cross-linked cellulosic material (or other absorbent material or materials) for the different layers of the absorbent core laminate rather than a single sheet, or by providing the laminate with additional layers.

C. The Backsheet

The backsheet 40 prevents the exudates absorbed and contained in the absorbent core 42 from wetting articles which contact the sanitary napkin 20 such as the wearer's pants, pajamas and undergarments. The backsheet 40 is impervious to liquids (e.g., menses and/or urine). The backsheet 40 is preferably manufactured from a thin plastic film, although other flexible liquid impervious materials may also be used.

The backsheet 40 may comprise a woven or nonwoven material, polymeric films such as thermoplastic films of polyethylene or polypropylene, or composite materials such as a film-coated nonwoven material. Preferably, the backsheet 40 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Film Products of Terre Haute, Ind., under the designation XP-39385.

The backsheet 40 is preferably embossed and/or matte finished to provide a more clothlike appearance. Further, the backsheet 40 may permit vapors to escape from the absorbent core 42 (i.e., the backsheet 40 may be breathable) while still preventing exudates from passing through the backsheet 40. Flushable or biodegradable backsheets can also be used, e.g., such as with pantiliner devices of the type described herein.

D. The Braided Wicking Structure

FIGS. 1 and 2 show that the sanitary napkin comprises at least one braided wicking component, such as braided wicking structure (or "braided structure") 44. The sanitary napkin 20 preferably comprises three separate braided structures 44A, B and C that are positioned between the absorbent core 42 and the backsheet 40. The braided structures shown in FIGS. 1 and 2 have a tubular cross-section and are stacked in a pyramid-like arrangement. The braided structures 44 are preferably centered along the longitudinal centerline of the sanitary napkin.

The term "braided structure", as used herein, refers to structures made by intertwining several strands of material 54. Preferably, the braided structures used in the present invention comprise three or more strands, and typically about five or six strands of material. The braiding can be used to form a tape, cord, string, or twine-like structure. In the present invention, the strands of material 54 that are braided to form the braided wicking structures preferably comprise a sliver or tow comprised of many individual fibers 56. The slivers or tows are each twisted to form the strands 54 that will be incorporated into the braided structure 44. The slivers or tows can be comprised of any suitable number of fibers and may be of any suitable size. In preferred embodiments, the individual fibers preferably have a denier per fiber of between about 1 and about 3, and the slivers or tows comprise several hundred individual fibers 56 (for example, around 400 fibers) and have a total denier of between about 100 to about 2,500.

The strands of material 54 forming the braided structure (and, thus the overall braided structure 44) can be either hydrophobic, or hydrophilic. Hydrophobic materials are suitable for use in the braided wicking structure 44 since liquids are transported through the spaces between the strands 54. Alternatively, some of the strands 54 can be hydrophobic and some of the strands can be hydrophilic (in which case the braided structure 44 would be partially hydrophobic and partially hydrophilic). The strands 54 comprising the braided structure 44 can all be made of a single material, or they can comprise different materials.

The fibers 56 comprising the strands 54 are preferably non-porous and hydrophobic so that liquids will not be absorbed into the interiors of the fibers. The surfaces of the fibers 56 may either be hydrophobic or hydrophilic. Preferably, however, in order for the fibers in the strands 54 that make up the braided structures to more easily move sufficient quantities of liquids, the surfaces of the fibers are hydrophilic. The surfaces of the fibers 56 forming the strands 54 of the braided structure are preferably either naturally hydrophilic or treated (such as by a surfactant) to render the same hydrophilic. In addition, the braided structures 44 can comprise fibers 56 having capillary channels which are wetted by the liquids, such as blood and urine, that are required to be transported. The fibers 56 comprising the strands may be smooth, or they may be textured (that is, they may have fibrils projecting from their surfaces). The fibers 56 can be made of materials such as polyethylene, polypropylene, polyester, cotton, rayon, ORLON, or any other suitable natural or synthetic materials. In preferred embodiments, the strands 54 comprise polypropylene fibers.

The fibers 56 and the strands 54 comprising the braided structure 44 are both preferably arranged in a continuous mode between the ends of the braided structure 44. The fibers and strands of the braided structure 44 should be aligned close enough together to form wicking channels. The strands 54 forming the braided structure 44 can have any suitable cross-sectional shape. Suitable cross-sectional shapes include, but are not limited to circular, oval, square, flat, triangular, irregular, etc. The strands 54 comprising the braided structure can all have the same cross-sectional shape, or they can have different cross-sectional shapes.

The braided structure 44 has a length and a width. The length of the braided structure 44 can vary according to the product needs and design. The length of the braided structure 44 preferably ranges from between about 1 inch (about 2.5 cm) to the length of the sanitary napkin (or other absorbent article). The radius of the braided structure 44 is the dimension, R, from the central axis, A, of the braided structure to the side wall of the braided structure (that is, ½ the actual width, W, of the braided structure). The radius, R, of the braided structure 44 typically ranges from about 0.05 inch (about 0.13 cm) to about 1 inch (about 2.5 cm), and preferably ranges from about 0.1 inch (about 0.3 cm) to about 0.5 inch (about 1.3 cm). The actual width, W, thus, preferably ranges from about ¼ inch to 1 inch (about 0.6 cm to about 2.5 cm). If there is more than one braided structure, the individual braided structures may be of the same size, or different sizes.

Figure 3:
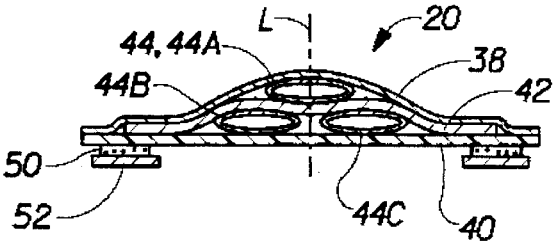
FIG. 3 is a cross section taken from an angle similar to that of FIG. 2 showing a sanitary napkin having braided wicking structures in an alternative arrangement.
Figure 5:
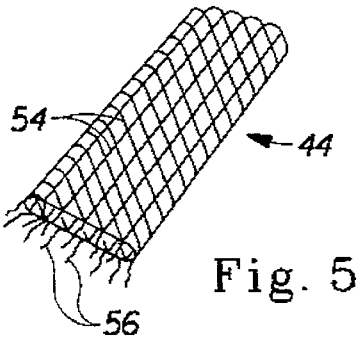
FIG. 5 is a perspective view of a portion of a flat braided structure.
Figure 4:
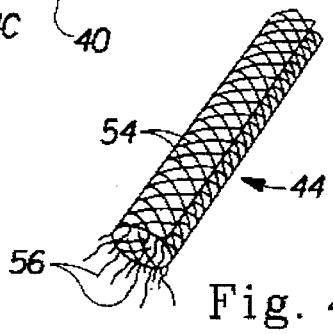
FIG. 4 is a perspective view of a portion of a conventional braided structure.
Figure 6:
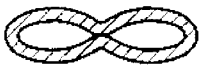
FIG. 6 is a cross-sectional view of a braided wicking structure having a "FIG. 8" cross-sectional configuration.

The braided wicking component 44 can be formed of a single braided structure or multiple braided structures (e.g., multiple parallel braided structures such as those shown in FIGS. 1–3). The braided structures used in the present invention can have many possible overall configurations. These include, but are not limited to conventional braided structures (such as those shown in FIG. 4); braided structures having an overall generally circular cross-sectional configuration, a flattened circular or elliptical cross-section; flat braided structures (shown in FIG. 5); braided structures having a cross-section in the shape of a "FIG. 8" (shown in FIG. 6); braided or other types of structures inside of braided structures; and tubular braided structures that have a hole down the center (FIGS. 1–3). Flat braided structures include those that are initially formed as flat structures and those that are cut and opened into flat structures.

The braided structure 44 is preferably kept in close contact with the component of the sanitary napkin that deposits liquids on the braided structure. In addition, at least the ends of the braided structure are preferably kept in close contact with the absorbent core 42, in order to efficiently transfer liquids to the absorbent core 42. This can be achieved by a number of suitable mechanisms. These include, but are not limited to maintaining the braided structure 44 in contact with the adjacent components, such as the absorbent core as by tensional forces, or by bonding it to these other components of the sanitary napkin by adhesives, and the like. A detailed description of suitable adhesives for this purpose and adhesive application configurations are found in the patent publications incorporated by reference herein.

The braided wicking structure 44 preferably functions as follows when it is positioned underneath the absorbent core. Liquid exudates will typically be deposited in a central region of the absorbent core 42. Some of the liquids deposited on the absorbent core 42 will be absorbed by the core. Other liquids will pass through the absorbent core 42 where they will contact the braided wicking structure 44. These liquids will be transported by the braided wicking structure 44 to portions of the absorbent core which have additional capacity. Cores typically exhibit high suctional forces which tend to draw away liquids from the braided structure 44 for ultimate storage and this results in the liquids distributed by the braided structure 44 being surrendered to the absorbent core. The absorbent core 42, thus, serves as a reservoir for liquids which are transferred from the braided structure 44. This at least partially "renews" the braided structure 44 for the next infusion of liquids.

There are several advantages of using a braided wicking structure. The braided structure 44 provides an acquisition/distribution structure with a more well-defined wicking channels in comparison to batts of fibers and nonwoven webs currently used for wicking liquids. The braided structure has well-defined capillaries between its strands. The braided structure also provides an overall structure that has a more well-defined shape (that is, sides and ends with more well-defined wicking characteristics in that liquids primarily wick toward the ends of the structure) so that it can be used to more accurately direct liquid exudates to any desired part of the sanitary napkin.

The braided structure is advantageous in that it can transport liquids on the surface of the strands, or it can transport liquids between strands. The ability of the braided structure to transport liquids between strands allows the braided structure to function similarly to capillary channel fibers with regard to the liquid wicking properties of the braided structure. That is, the wicking properties are dependent on the relatively fixed spacing between the strands, rather than on some spacing that could be subject to change under pressure, such as the capillary spaces between the fibers in a nonwoven fabric or batt of fibers. This allows for easy and fast acquisition of liquids, and for the transportation of liquids under pressure, such as the pressures associated with the weight of the wearer's body and other forces exerted on the sanitary napkin during wear. Thus, while wicking structures in the form of webs or batts of fibers are able to transport volume of liquids in the range of 0.01 to 0.045 cc/second when they are not subjected to pressure, their witking ability decreases dramatically when placed under such pressures. The braided wicking structure used in the present invention, on the other hand, can still transport such quantities of liquids (e.g., 0.033 grams/second) when under pressures as great as 1 psi (such as those applied by an adult's body).

The braided structure provides still other advantages for transporting liquids. The braided structure can transport liquids between like materials, or it can transport liquids from one type of material to another. In addition, it is believed that the braided structures described herein are capable of transporting liquids having a range of viscosities. These braided structures are particularly suitable for transporting liquids of low to medium viscosities (such as liquids having viscosities ranging from that of menstrual fluid to urine). It is also believed that braided structures will easily dewater into higher suction (higher capillary force) materials, and will continue to drain themselves of liquids until almost all of the liquids have been moved through the spaces between the strands.

A further advantage of the present invention is that the braided structures are generally relatively soft and flexible. In addition, the fibers formed into the braided structures, and the braided structures formed thereby, are relatively easy to make and also to handle and process (that is, to manufacture into absorbent articles).

Many alternative embodiments to the sanitary napkin shown in FIGS. 1 and 2 are possible. The braided structure 44, as shown in FIG. 1, can be oriented in the longitudinal direction and centered relative to the transverse centerline, T, of the sanitary napkin. In alternative embodiments, however, the braided structure 44 can be offset from the transverse centerline (that is, positioned forward or rearward of the transverse centerline). If the braided structure 44 is offset from the transverse centerline, it is preferably positioned so that it at least partially lies in the central region 32 of the sanitary napkin 20. In still other embodiments, the braided structure 44 can be oriented in any other direction needed to move liquids within the sanitary napkin.

The braided structure 44 can, as shown in FIGS. 1 and 2, be positioned between the absorbent core 42 and the backsheet 40. In other alternative embodiments, the braided structure can be positioned between the topsheet 38 and the absorbent core 42, within the absorbent core, or partially within a component such as the core and partially outside of such a component. The braided structure is preferably positioned on top of the absorbent core when the absorbent core comprises a laminate. This is because laminate structures are often less pervious to liquids in the Z-direction (i.e., through their thickness) than non-laminate structures, so unless the braided structure is on top of the core, liquids will have difficulty reaching the braided wicking structure making it difficult for the braided structure to carry out its wicking function. When the braided structure 44 is positioned on top of the absorbent core, the braided structure 44 can be positioned in close contact with the wearer's body. Even more advantageously, the braided structure 44 can be of such a size and shape that it (along with any overlying components) can fit at least partially within the space between the wearer's labia. This will allow it to more readily intercept exudates that leave the wearer's body.

In other alternative embodiments, the braided structure 44 can also serve as a topsheet, or as a portion of the topsheet. In still other alternative embodiments, the braided structure 44 can be used to store bodily exudates (in addition to, or instead of the separate absorbent core). The braided structures described herein are believed to be useful in serving liquid storage functions since they may be capable of storing up to about ten times their weight of bodily liquids, or more, as they move liquids toward the desired storage place. Thus, while the fibers 56 of the braided structure 44 are typically nonabsorbent (that is, they do not absorb liquids into their interiors), and although the braided structure typically transfers liquids into higher suction components, if the braided structure 44 is placed into an absorbent article in which no such higher suction components are present, the braided structure 44 will store the body liquids. In yet other embodiments, the braided structure 44 can serve the functions of more than one other component of the sanitary napkin.

E. Assembly of the Components of the Sanitary Napkin and Use of the Sanitary Napkin The components of the sanitary napkin such as the topsheet, the backsheet, the braided structure, the absorbent core, and any other components, may be assembled in a variety of well known configurations (including "sandwich" configurations, "tube" configurations, and configurations having side flaps).

The components of the sanitary napkin are preferably assembled in a "sandwich" configuration with the topsheet, backsheet, and absorbent core each comprising a layer, with the absorbent core positioned between the topsheet and backsheet and the braided structure in contact with the absorbent core. The topsheet and backsheet are preferably sized so that their peripheries extend beyond the periphery of the absorbent core, and are sealed together by a perimeter seal 90.

The components of the sanitary napkin 20 may be held together in any suitable manner. The components of the sanitary napkin 20 can be secured together by adhesives, stitching, heat and/or pressure bonds, dynamic mechanical bonds, ultrasonic bonds, intermingling or entanglement of the fibers or other structural elements comprising the components of the sanitary napkin, such as by meltblowing the fibers comprising one component onto another component, or by any other means known in the art. Suitable means for attaching the components of the sanitary napkin are described in the patent applications and publications incorporated by reference herein.

The sanitary napkin 20 of the present invention is used by removing any release liner 52 and thereafter placing the sanitary napkin 20 in a panty so that the adhesive (or other fastener) 50 contacts the panty and maintains the sanitary napkin in position within the panty during use.

F. Optional Features and Alternative Types of Absorbent Articles

While preferred sanitary napkin embodiments of the present invention have been described, numerous other sanitary napkins are disclosed in the literature. These could also be provided with the braided wicking structure of the present invention. Several such sanitary napkins are disclosed in U.S. Pat. No. 4,321,924, "Bordered Disposable Absorbent Article" issued to Ahr on Mar. 30, 1982; U.S. Pat. No. 4,425,130, "Compound Sanitary Napkin" issued to DesMarais on Jan. 10, 1084; the aforementioned U.S. Pat. No. 4,950,264 issued to Osborn on Aug. 21, 1990, U.S. Pat. No. 5,007,906 entitled "Decoupled Sanitary Napkin" issued to Osborn, et al. on Apr. 16, 1991, the aforementioned U.S. Pat. No. 5,009,653 issued to Osborn on Apr. 23, 1991; U.S. Pat. No. 5,308,346 entitled "Elasticized Sanitary Napkin" issued to Sheller, et al. on May 3, 1994; and, U.S. Pat. No. 5,324,278 entitled, "Sanitary Napkin Having Components Capable of Separation in Use" issued to Visscher, et al. on Jun. 28, 1994.

In addition, the sanitary napkin having the braided wicking structure of the present invention may be made in accordance with the disclosures of the following pending U.S. patent applications which were filed on Jul. 23, 1992 (wherein the braided wicking structure could be substituted for, or used in addition to the capillary channel fiber structures): U.S. patent application Ser. No. 07/915,202, entitled "Curved, Shaped Absorbent Article" filed in the name of Theresa L. Johnson, et al. (PCT Publication No. WO 93/01781); U.S. patent application Ser. No. 07/915,285, entitled "Absorbent Article Having Resilient Center" filed in the name of Thomas W. Osborn, et al. (PCT Publication No. WO 93/01782); U.S. patent application Ser. No. 07/915,201, entitled "Absorbent Article Fastener Pattern" filed in the name of Robb E. Olsen, et al. (PCT Publication No. WO 93/01783); and, U.S. patent application Ser. No. 07/915,134, entitled "Method of Making Curved, Shaped Absorbent Article" filed in the name of Letha M. Hines, et al. (PCT Publication No. WO 93/01784).

The sanitary napkin 20 may also be provided with a pair of flaps, each of which extends laterally outward along a side edge of the main body portion of the sanitary napkin. A number of sanitary napkins having flaps suitable or adaptable for use with the sanitary napkin 20 of the present invention are known. Such flaps are disclosed in U.S. Pat. No. 4,285,343 entitled "Sanitary Napkin", issued to McNair on Aug. 25, 1981; U.S. Pat. No. 4,589,876 entitled "Sanitary Napkin", issued to Van Tilburg on May 20, 1986; and, U.S. Pat. No. 4,687,478, entitled "Shaped Sanitary Napkin With Flaps", issued to Van Tilburg on Aug. 18, 1987. Some particularly preferred types of flaps are described in U.S. Pat. No. 5,281,209 entitled "Absorbent Article Having Tucked Flaps" issued to Osborn, et al. on Jan. 25, 1994, and in allowed U.S. patent application Ser. No. 08/073,256 entitled "Absorbent Article Having Flaps and Zones of Differential Extensibility" filed in the name of Lavash, et al. on Jun. 4, 1993 (PCT Publication WO 93/06805, published Apr. 15, 1993).

The sanitary napkin described herein can also be comprised one or more extensible components. In one preferred embodiment, most or all of the components are extensible to provide a degree of extensibility (on the order of 15%–40%) to the entire sanitary napkin. This extensibility may provide better in-use fit and comfort. Suitable extensible absorbent articles are described in U.S. patent application Ser. No. 07/915,133, entitled "Stretchable Absorbent Articles" filed in the name of Osborn, et al. on Jul. 23, 1992 (PCT Publication No. WO 93/01785 published Feb. 4, 1993).

The terms "panty liner" or "pantiliner" refer to absorbent articles that are less bulky than sanitary napkins which are generally worn by women between their menstrual periods. Suitable absorbent articles in the form of pantiliners which could be provided with a braided wicking structure are disclosed in U.S. Pat. No. 4,738,676 entitled "Pantiliner" issued to Osborn on Apr. 19, 1988.

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinence articles that can be provided with the braided wicking structure distribution described herein are disclosed in U.S. Pat. No. 4,253,461 issued to Strickland, et al. on Mar. 3, 1981; U.S. Pat. Nos. 4,597,760 and 4,597,761 issued to Buell; U.S. Pat. No. 4,909,802 issued to Ahr, et al.; U.S. Pat. No. 4,964,860 issued to Gipson, et al. on Oct. 23, 1990; U.S. Pat. No. 5,300,054 issued to Feist, et al.; and, U.S. Pat. No. 5,304,161 issued to Noel, et al.

The term "diaper" refers to absorbent articles worn by infants and incontinent persons that are fastened about the waist of the wearer. Suitable diapers that can be provided with the braided wicking structure of the present invention are disclosed in U.S. Pat. No. 3,860,003 issued to Buell on Jan. 14, 1975, and U.S. Pat. No. 5,151,092 issued to Buell, et al. on Sep. 29, 1992.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a longitudinal centerline, two longitudinal side edges, and two transverse end edges, said absorbent article comprising:

a liquid pervious topsheet;

a liquid impervious backsheet joined to said topsheet;

an absorbent core positioned between said topsheet and backsheet; and a braided wicking structure positioned between said topsheet and said backsheet, said braided wicking structure having a pair of ends and being comprised of strands comprised of a twisted tow, said tow comprising a plurality of substantially non-absorbent fibers, wherein said fibers have, in cross section, a substantially regular geometric shape and said ends of said braided wicking structure are in contact with said absorbent core.

* * * * *